United States Patent
Fletcher et al.

(10) Patent No.: US 10,542,885 B2
(45) Date of Patent: Jan. 28, 2020

(54) RETINAL CELLSCOPE APPARATUS

(71) Applicant: THE REGENTS OF THE UNIVERSITY OF CALIFORNIA, Oakland, CA (US)

(72) Inventors: Daniel Fletcher, Berkeley, CA (US); Robi Maamari, St. Louis, MO (US); Neil Switz, Oakland, CA (US); Todd P. Margolis, Kentfield, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 76 days.

(21) Appl. No.: 15/094,750

(22) Filed: Apr. 8, 2016

(65) Prior Publication Data

US 2016/0296112 A1 Oct. 13, 2016

Related U.S. Application Data

(63) Continuation of application No. PCT/US2014/060184, filed on Oct. 10, 2014.
(Continued)

(51) Int. Cl.
*A61B 3/14* (2006.01)
*A61B 3/12* (2006.01)
*A61B 3/00* (2006.01)

(52) U.S. Cl.
CPC .............. *A61B 3/14* (2013.01); *A61B 3/0025* (2013.01); *A61B 3/0091* (2013.01); *A61B 3/12* (2013.01)

(58) Field of Classification Search
CPC .... A61B 3/10; A61B 3/12; A61B 3/14; A61B 3/15; A61B 3/0025; A61B 3/0091;
(Continued)

(56) References Cited

U.S. PATENT DOCUMENTS

| 5,406,342 A | 4/1995 | Jongsma |
| 2003/0156258 A1 | 8/2003 | Tanassi |

(Continued)

FOREIGN PATENT DOCUMENTS

| WO | 2015054672 A1 | 4/2015 |
| WO | 2017180965 A1 | 10/2017 |

OTHER PUBLICATIONS

ISA/KR, Korean Intellectual Property Office (KIPO), International Search Report and Written Opinion dated Jan. 22, 2015, related PCT international application No. PCT/US2014/060184, pp. 1-13, claims searched, pp. 14-18.

(Continued)

*Primary Examiner* — Mustak Choudhury
(74) *Attorney, Agent, or Firm* — O'Banion & Ritchey LLP; John P. O'Banion (57) ABSTRACT

A handheld, ocular imaging device and system that employs the camera, processor and programming of a mobile phone, tablet or other smart device coupled to optical elements and illumination elements that can be used to image the structures of the eye in home-based, ambulatory-care, hospital-based, or emergency-care settings, is presented. The modular device provides multi-functionality (fluorescein imaging, fluorescence, brightfield, infrared (IR) imaging, near-infrared (NIR) imaging) and multi-region imaging (retinal, corneal, external, etc.) of the eye along with the added features of image processing, storage and wireless data transmission for remote storage and evaluation. Acquired ocular images can also be transmitted directly from the device to the electronic medical records of a patient without the need for an intermediate computer system.

19 Claims, 4 Drawing Sheets

Related U.S. Application Data (60) Provisional application No. 61/889,084, filed on Oct. 10, 2013.

(58) Field of Classification Search
CPC ......... A61B 3/107; A61B 3/152; A61B 3/156; A61B 3/185; A61B 3/1208; A61B 3/1241; H04N 5/33; H04N 5/2254; H04N 5/2256; H04N 5/2354; G01B 11/25; G01B 11/255; G01B 11/2531; G01B 2210/14
USPC ..... 351/200–218, 221, 246; 348/78, E5.045, 348/E7.085; 356/604
See application file for complete search history.

(56) References Cited

U.S. PATENT DOCUMENTS

| | | | |
|---|---|---|---|
| 2005/0041207 A1* | 2/2005 | Miller | A61B 3/156 351/200 |
| 2005/0270484 A1 | 12/2005 | Maeda et al. | |
| 2008/0002152 A1 | 1/2008 | Collins et al. | |
| 2011/0279776 A1 | 11/2011 | Spaide | |
| 2012/0050672 A1 | 3/2012 | Aikawa | |
| 2012/0229617 A1* | 9/2012 | Yates | A61B 3/156 348/78 |
| 2013/0135584 A1* | 5/2013 | Alasaarela | A61B 3/1208 351/206 |
| 2015/0002817 A1 | 1/2015 | Alasaarela | |
| 2015/0335239 A1 | 11/2015 | MacFougall | |

OTHER PUBLICATIONS

ISA/KR, Korean Intellectual Property Office (KIPO), International Search Report and Written Opinion dated Apr. 14, 2017, related PCT international application No. PCT/US2017/027572, pp. 1-13, claims searched, pp. 14-19.

* cited by examiner

RETINAL CELLSCOPE APPARATUS

CROSS-REFERENCE TO RELATED APPLICATIONS

This application is a 35 U.S.C. § 111(a) continuation of PCT international application number PCT/US2014/060184 filed on Oct. 10, 2014, incorporated herein by reference in its entirety, which claims priority to, and the benefit of, U.S. provisional patent application Ser. No. 61/889,084 filed on Oct. 10, 2013, incorporated herein by reference in its entirety. Priority is claimed to each of the foregoing applications.

The above-referenced PCT international application was published as PCT International Publication No. WO 2015/054672 on Apr. 16, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND

1. Technical Field

This technology pertains generally to ocular diagnostic imaging devices, and more particularly to a portable handheld smart phone-based retinal camera, capable of capturing high-quality, wide field fundus images. The use of the mobile phone platform creates a fully embedded system capable of acquisition, storage, and analysis of fundus images that can be directly transmitted from the phone via the wireless telecommunication system for remote evaluation.

2. Background Discussion

Since the late $19^{th}$ century, when retinal imaging was first described, there has been steady technical improvement in imaging of the fundus of the eye. Digital fundus imaging is used extensively in the diagnosis, monitoring, and management of many retinal diseases. Access to fundus photography is often limited by patient morbidity, high equipment cost, and a shortage of trained personnel. Direct ophthalmoscopes, binocular indirect ophthalmoscopes, and funduscopic cameras are the standard of care for ocular examination and these devices can cost as much as $30,000 each.

One limitation found in current imaging systems is the bulky and stationary nature of the equipment. Standard fundus cameras are cumbersome tabletop devices that are not readily mobile due to the fragility, large size and heavy weight of these devices. Current tabletop fundus cameras also require the patient to be seated upright, which can be difficult for sick and hospitalized patients.

In addition to dimensional constraints, fundus cameras require a power source to supply power to the illumination, imaging screen, and data processing unit. Often this power source is provided by central in-wall power plugs, and continuous electrical power is required in order for the fundus camera to function properly.

An additional factor that increases the size and cost of current fundus imaging devices is the use of dedicated camera modules, dedicated computing systems, and dedicated storage systems for the capture, processing, and storage of the acquired fundus images.

Technical limitations also exist in fundus photography with current devices. Special consideration must be taken in order to obtain high quality images with limited reflections from the optical components of the system and the anatomical surfaces of the eye. Often, additional features and components are included in the optical system for the specific purpose of reducing system reflections. For example, some devices use a black dot lens to limit the reflection off of the lens in the system as well as the use of an apertured mirror to limit the reflection from the corneal surface.

The field of view of the retina is another technical specification of fundus imaging that is an important consideration in fundus camera development. Field of view describes the angle through the pupil at which the retina is imaged. The illuminating light from the device enters the retina and the reflected light from the retina is used to form an image on the sensor of the device. Many devices offer limited fields of view due to the increased complexity associated with wider fields. For example, typical direct ophthalmoscopes have a 5-degree field of view compared to a 45-degree field of view of standard fundus cameras.

Binocular indirect ophthalmoscopes produce an inverted image that is viewed by an ophthalmologist. Although ophthalmologists are trained to use this equipment, the use of a device that produces an inverted image is often difficult to use by the untrained user since it is not intuitive.

Finally, current standard bench top fundus cameras require the use of a dedicated computing system (i.e. computer, laptop, or any other secondary device) to receive and process the images.

Accordingly, there is a need for a low cost handheld device that can function as a substitute for these high cost medical devices, enabling the recording of digital images of the ophthalmic exam by both experts and non-experts that is also capable of transmitting these images for expert evaluation.

BRIEF SUMMARY

The technology described herein provides an apparatus and methods for digital ocular imaging incorporating a mobile device-based retinal camera that leverages the compact size, high-resolution camera, large data storage capacity, and wireless data transfer capabilities of current mobile devices to capture diagnostic retinal images. The device is preferably a modular system with an interchangeable lens arrangement and camera attachment that enables imaging of different regions of the eye, including the retina, the anterior segment, the cornea, as well as other external parts of the eye such as the eyelid and sclera.

In various embodiments, a handheld, ocular imaging device is provided that employs the camera of a mobile phone. The ocular imaging device includes lenses, illumination sources, and/or other optical elements that are connected to a mobile phone, which is used for image capture, processing, storage, and/or transmission.

In one embodiment, the camera includes a custom-designed mobile phone attachment that houses optics capable of capturing a retinal field-of-view of approximately 55 degrees. The device allows a completely portable and inexpensive system for retinal imaging that could be used both in a hospital setting as well as for community eye screening.

The handheld, modular device provides multi-functionality (fluorescein imaging, fluorescence, brightfield (white light), infrared (IR) imaging, near-infrared (NIR) imaging etc.) and multi-region imaging (retinal, corneal, external, etc.) along with the added features of wireless data transmission and portability, and can serve as a substitute for high cost tools (i.e. slit lamps, binocular indirect ophthalmoscopes, funduscopic cameras, fluorescein imaging cameras, etc.) in regions that require low cost, portable, and more-inclusive tools. The individual imaging modalities can function independently or they can be combined as a "toolkit" to include two or more interchangeable imaging tools.

Diagnosis and examination of ocular injury or disease is done through a comprehensive evaluation of various regions of the eye, including the retina, anterior segment (cornea, iris, lens, etc.), and the external features (eyelid, conjunctiva, etc.) for a virtual representation of the eye. Evaluation can be done: (a) at the site of image acquisition by visual inspection of the images on the mobile device; (b) at the site of image capture via image processing done on the mobile device; or (c) remotely through wireless transmission (data, Wi-Fi, Bluetooth, etc.) of the images to an on-site or off-site/remote computer for evaluation by image processing or by a trained individual.

The handheld devices may be used in hospitals, clinics, and physician offices to examine patients outside of the typical ophthalmology setting. For example, primary care physicians can use the device to image the eyes of a patient and wirelessly upload the images via the mobile device interface for consultations from eye specialists. With approximately 314 million people worldwide visually impaired, and, with 87% of the affected population residing in developing countries, many of the diseases affecting these individuals could be diagnosed easily and treated if proper healthcare facilities exist that can provide proper eye examinations for screening of these diseases.

The wireless device can aid in an emergency care setting via remote consultation if eye specialists are not immediately available at a particular location. The handheld device can also be used for immobile inpatients in the hospital as a tool for bedside image acquisition.

With the current movement towards electronic medical records (EMRs), the device can serve as an all-inclusive tool to capture and upload ocular images directly to the patients EMR directly from the mobile device without the need for an intermediate computer system. The technology provides a low cost handheld device that can function as a substitute for conventional high cost medical devices, enabling the recording of digital images of the ophthalmic exam by both experts and non-experts and transmitting these images for remote expert evaluation.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Figure 1:
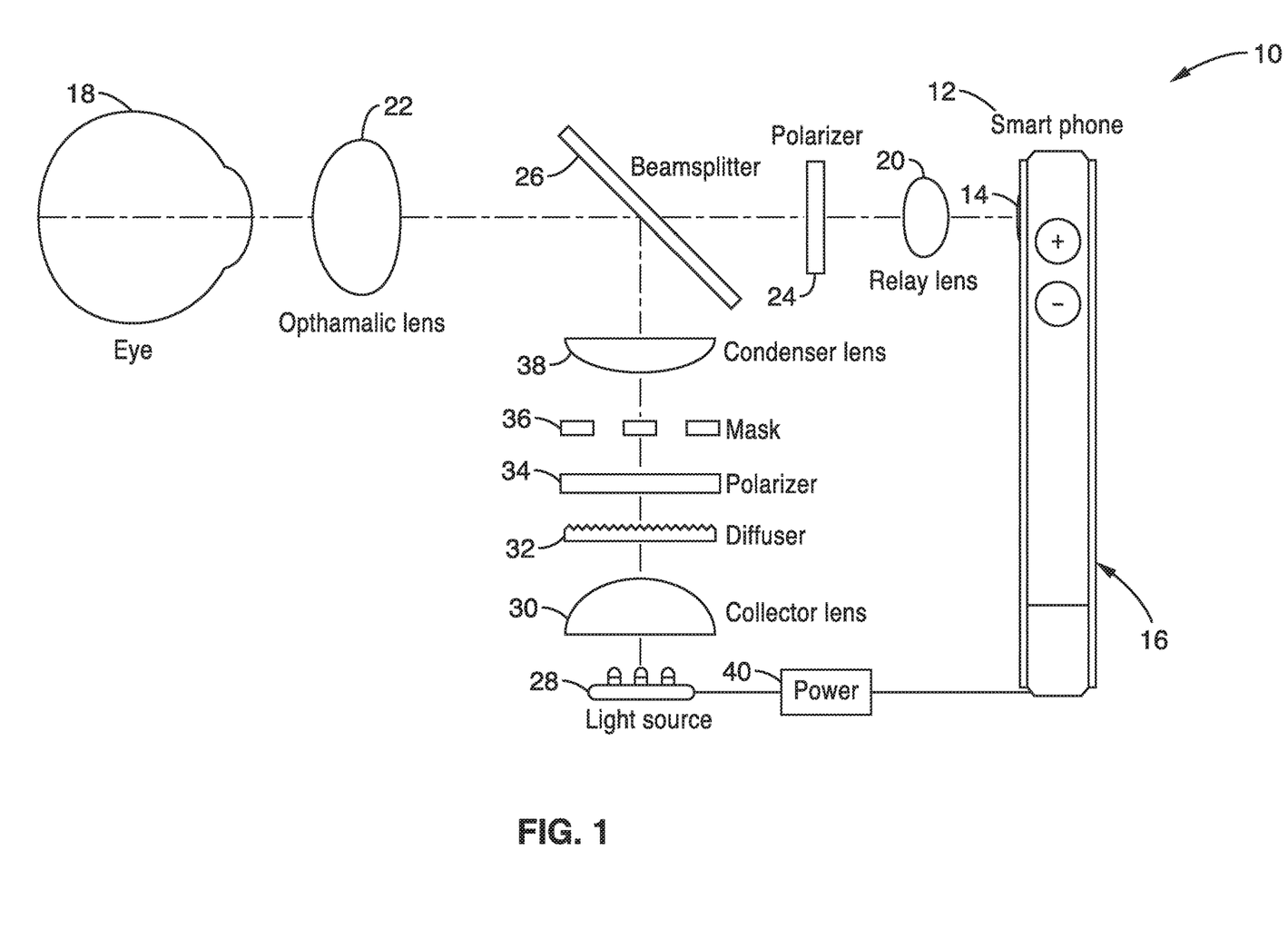
FIG. 1 is a schematic component drawing of one embodiment of the apparatus.
Figure 2:
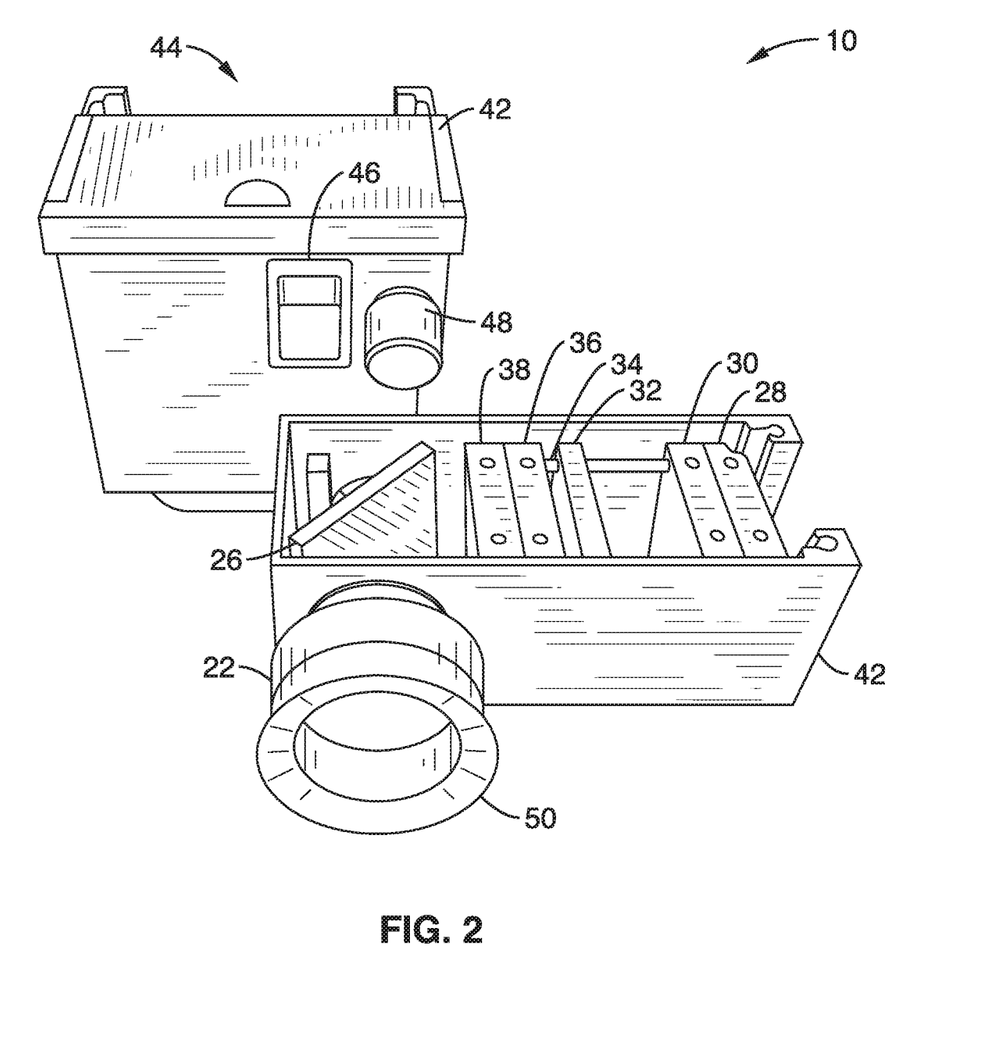
FIG. 2 is a front perspective view of an embodiment of the apparatus with the top part of the housing removed to show the interior.

Turning now to FIG. 1, one embodiment of a mobile retina imaging apparatus 10 is schematically shown and an apparatus configured with the elements shown in FIG. 1 is shown in FIG. 2. By way of example, and not of limitation, the apparatus 10 generally uses optics and the camera, processor, and the wireless capabilities of a mobile device 12 to create a fully embedded system that eliminates the need for a separate computing system to transfer and store acquired images. The system can be used for fundus imaging without the need for an ophthalmoscope.

The mobile device 12 is preferably a smart phone or tablet that is capable of wireless as well as Bluetooth types of communications through existing telecommunications networks and devices. Although a remote communications capability is preferred, it is not essential and the acquired images can be stored in the device on permanent or removable media and accessed at a later time for evaluation.

Typically the camera feature of a mobile device 12 has a camera lens 14 and display 16 that permits an initial visualization of views presented through the camera lens 14. Specific images can be obtained by pressing a button on the mobile device 12 or device display 16. The structures of the eye 18 of the test subject are viewed by the camera of the mobile device 12 through a coordinated pair of lenses or groups of lenses that together provide an objective lens. In the embodiment shown in FIG. 1, the lens 14 of the mobile device 12 is aligned with a relay lens 20 and an ophthalmic lens 22 illustrated with a dashed line in order to visualize and image the retina and other eye structures.

The relay lens 20 and an ophthalmic lens 22 are preferably mounted at a distance equal to the sum of the focal lengths of lens 20 and lens 22 from each other. The lenses 20, 22 can be single lenses or comprise multiple lenses coupled or cemented together.

The relay lens 20 and the ophthalmic lens 22, or similarly positioned compound lenses, can produce a field-of-view that is greater than a direct ophthalmoscope, and equivalent or greater than the standard tabletop ophthalmoscope.

The selection of the dimensions of relay lens 20 will be influenced by the ophthalmic lens 22 as well as the optical characteristics and capabilities of the mobile phone or camera. The larger the focal length of the relay lens, the less magnification of the image of the retina onto the sensor of the camera. Therefore, the lens characteristics are preferably selected to capture the full field of view generated by the ophthalmic lens so that it is circumscribed onto the sensor of the camera. However, alternative configurations can be selected where the smaller focal length of the relay lens would create higher magnification of the retina in other embodiments.

For example, in one embodiment, the relay lens 20 is preferably an achromatic lens with a 12.5 mm diameter and a 20 mm focal length that consists of two optical components made up of S—BaH11/N—SF10 substrate cemented together to form an achromatic doublet. The ophthalmic lens 22 is preferably a 54 diopter double-aspheric lens designed for use in indirect ophthalmoscopy with the slit lamp.

To minimize reflections within the system, optional polarizer's can be used. One polarizer can be placed in the illumination path, and a second polarizer will be crossways to the first polarizer and placed in the imaging path. Accordingly, in the embodiment shown in FIG. 1, a polarizer 24 is positioned in the imaging path.

A beam splitter 26 is also placed at approximately a 45-degree angle in the imaging path to reflect light from an illumination path towards the eye 18 of the subject. In addition, a polarizing beam splitter 26 may also be used to decrease reflections, in one embodiment.

In the embodiment shown in FIG. 1, the eye 18 is illuminated with a light source 28 that is preferentially reflected from the beam splitter 26 to illuminate the structures of the eye 18 through the ophthalmic lens 22. For illumination in the system, a light source 28 is provided that can be configured to produce light at selected wavelengths and intensities. For example, the light source can be made from one or more light-emitting diodes or other light sources and the light source may also use fiber optic cables to deliver light. The LEDs can also be white, red, infrared, blue, green, or any combination of colors.

The light source 28 can also be monochromatic or use lights in any combination of colors or patterns. The light source 28 can be connected by a wire or cable to a power source and circuit 40 that can be powered by the battery of the mobile device 12 or by an external battery. The light source 28 can also be controlled by a wireless connection with the mobile device 12 through the Bluetooth or Wi-Fi capabilities of the mobile device. The light source 28 preferably has one or more light emitters that can be individually controlled.

The light emitted from the light source 28 is collected with a collecting lens 30 that is located at a distance approximately equal to the focal length of the lens 30.

A diffuser 32 is located in front of the collecting lens 30 and the condensed beam. The diffuser 32 can be constructed from ground glass, plastic, or any other substrate that will allow for near-uniform illumination. The diffuser ensures that the light emissions from high intensity LEDs are not directly imaged onto the retina.

A polarizer 34 is placed in the illumination path in front of the diffuser 32. The polarizer 34 is preferably positioned in such a manner that the polarization of the illumination light that is ultimately incident on the beam splitter 26 is in the s-polarization. In another embodiment, the mask 36, is placed in front of the diffuser 32 rather than the polarizer 34.

Figure 3:
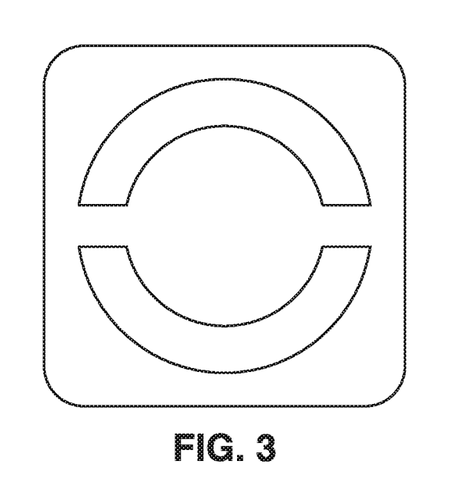
FIG. 3 is an example of one mask design with an annular pattern.

Light through the polarizer 34 is directed through a mask 36 that can be of any design. Using mask 34, any desired pattern can be imaged onto the cornea of the eye 18 of the subject. For example, an annular pattern, such as shown in FIG. 3, can be used to create a magnified or de-magnified image of the annulus on the cornea of the subject depending on the optics.

Patterned light is condensed through a condenser lens 38 in the illumination path. Light emerging from the condenser lens 38 is directed to one face of the beam splitter 26.

The beam splitter 26 is mounted at an angle such that the illumination reflecting off of it is directed through ophthalmic lens 22 to the eye 18. The combination of lens 30, lens 38, and lens 22, and the relative spacing between components are chosen such that the pattern of mask 36 is imaged onto or near the cornea of eye 18.

After traversing the cornea, the illumination from lens 22 travels through the anterior chamber of the eye 18, the dilated pupil, the lens of the eye, and the vitreous humour to the retina. The image of the mask 36 is chosen to be in focus at the cornea and of dimensions that allow the illumination light to pass through a peripheral region of the cornea and pupil into the vitreous humour to illuminate the retina.

In one embodiment, the retina is illuminated using a cone of light that enters the dilated eye at the periphery of the pupil to provide illumination, while imaging through the center of the pupil to additionally avoid pollution of the collected image with illumination light reflected, e.g., off the corneal surface.

Although the pupil of the subject is typically dilated, this is optional. In one embodiment the apparatus may be designed to image without dilation of the subject's pupil by automatically assembling multiple images of the retina captured by directing the gaze of the eye with fixation lights described below.

By imaging the illuminated mask pattern on the cornea, reflections off of the corneal and other surfaces that would otherwise corrupt the image of the retina are reduced. Different mask designs can be inserted to avoid reflections in different locations, such that a series of images of the retina could be collected and combined to create a single reflection-free image. For example, a set of masks within the optical system can be automatically or manually iterated to collect images with and without reflections in different parts of the image, so that the images can be combined to create one image with minimized reflections.

Furthermore, the image of the annulus of light is focused on the cornea and defocuses as it approaches the retina so that a uniform illumination onto the retina is created.

The annulus needs to be focused sufficiently to penetrate the cornea, anterior compartment, and lens while in focus, but defocused by the time it gets to the retina so that the illumination of the retina is uniform. The depth of focus of the illuminated annulus is determined by the numerical aperture (NA). Preferred numerical aperture values are selected from the group consisting of less than or equal to 0.01; less than or equal to 0.1; less than or equal to 0.25; less than or equal to 0.5; and less than or equal to 1.

The retina of the subject acts as a surface that depolarizes the incoming light. The depolarized light reflecting off of the retina then returns through the ophthalmic or objective lens 22.

Table 1 provides examples of the preferred image sizes of the various mask slit sizes that range from 7.0 mm to 10.0 mm. For example, using the pattern of FIG. 3, an 8.0 mm inner slit size can be chosen based on the assumption that a dilated pupil ranges from 6.0 mm to 8.0 mm to allow a range from a 1.0 mm annulus of light (6.0 mm [pupil]–5.0 mm [inner slit size]) to 3.0 mm annulus of light (8.0 mm [pupil]–5.0 mm [inner slit size]).

The returning reflected light through lens 22 is directed to the beam splitter 26. The properties of the beam splitter 26 are such that the rays in the P-polarization state are preferentially transmitted through the beam splitter along the imaging path shown in FIG. 1. The transmitted light through the beam splitter then travels through the imaging polarizer 24 that is positioned in the P-polarization state relative to the beam splitter 26. These rays then travel through lens 20 to the camera 14 of the mobile device 12. Any light that does not pass through the beam splitter may be collected in an optional light trap made from matte black paint, which can be painted on the interior housing surfaces behind the beam splitter to reduce reflection off the surfaces. The light trap can be felt, matte, conical design, flat black paint to minimize reflection of illumination light back to the image detector.

The rejection of light in the imaging path that is of the same polarization state as the illumination by the system is important because it acts as a method of reducing the artifacts created by reflections off of surfaces in the system. For example, light in the S-polarization state will reflect off of component surfaces including both sides of ophthalmic lens 22, the cornea, the relay lens 20, as well as any other surface where there is a change in the index of refraction. Since P-polarization relative to the beam splitter is preferentially transmitted through the beam splitter and/or subsequent optics in the imaging path, reflective artifacts in the S-polarization state off of the interfaces in the imaging path are reduced in the final image. The depolarization that occurs at the retina allows an image to be collected that is comprised mainly of rays in the P-polarization state relative to the beam splitter surface.

The imaging system shown in FIG. 1 can also include optional optical filters such as color glass filters or any type of interference filter (bandpass, longpass, shortpass, etc.) that are positioned within the imaging path. Such filters may also be contained in the mobile device 12, or through image processing.

Images of the structures of the eye 18 that are received by the mobile device 12 can be processed, stored or transmitted to remote servers or computers for storage and evaluation. The system can be configured for wired or wireless transmission methods including Wi-Fi, Bluetooth, cellular networks, and Ethernet.

FIG. 2 is an embodiment of the device shown schematically in FIG. 1 without the housing covers so that the internal components can be viewed. The housing 42 has a slot 44 for receiving the mobile device.

Preferably, the ocular device contains a coupling adaptor so that the lens system can be specifically built with a dedicated holder to align the camera lens 14 of the mobile device 12 with the optical axis of the ocular device. In FIG. 2, the mobile device is optically coupled to the first relay lens 20 by sliding the mobile device into the slot 44 of the ocular device housing 42. Although a slot type configuration is preferred, other methods for coupling the mobile device with the device housing can be used such as clipping the mobile device to the ocular device or magnetically aligning the devices and the two optical axes. The aligned axes of the housing optics and the mobile device provide a minified image of the retina to be imaged onto the sensor of the mobile device camera.

The housing 42 can be made from many different materials that are sturdy and rigid enough to maintain the alignment of the optics and to seal the optics from ambient light. For example, an acrylonitrile butadiene styrene plastic is a suitable material for the housing. However, housings made from other materials including other plastics, metals, or a combination of the two materials is possible.

In the embodiment shown in FIG. 2, there are generally two sections to the housing 42. The first section houses the relay lens 20 along with batteries and power circuits. The housing may have an on-off switch 46 for the device. A fine-tuning knob 48 may also be used to adjust the intensity of the light illumination system, the distances between the ophthalmic lens 22 and the relay lens 20, or between the various other lenses in the device.

The second section of the housing 42 contains the illumination components. The beam splitter 26 is at the junction between the imaging path and the illumination path. The illumination section of the housing 42 of the apparatus houses the optical components that can be positioned using cage plates designed for holding and mounting optical components. For instance, in one embodiment, cage plates accepting one inch optics can be used.

The illumination section of the housing 42 of FIG. 2 has light source 28, collector lens 30, diffuser 32, polarizer 34, mask 36 and condenser lens 38 components. The light source 28 is wired to a battery power source and circuit in the power section of the housing.

The ophthalmic lens 22 in this embodiment is designed to be interchangeable to enable different levels of magnification. The lens 22 can be in a plastic casing that is removable using a clipping system or a release button that enables an objective lens in the plastic housing to be removed when the clip or button are pressed. Another objective lens with a different power can then be attached to the housing and will remain stationary and fixed to the remainder of the ocular device.

The preferred interchangeable front lenses have a diopter selected from the group consisting of a Diopter≥1; a Diopter≥5; a Diopter≥10; a Diopter≥15; a Diopter≥30; and a Diopter≥50.

Preferred imaging systems have objective lenses to capture a field of view selected from the group consisting of Field-of-view>5 degrees; Field of view>10 degrees; Field-of-view>20 degrees; Field-of-view>25 degrees; Field-of-view>30 degrees; Field-of-view>45 degrees; Field-of-view>55 degrees; and Field-of-view>70 degrees.

The apparatus may also have one or more resting points for resting the system on the temporal, zygomatic, maxillary bone, or other parts of the orbit to provide stable imaging of the fundus. The rest(s) can be made of from a rigid material to fix the distance the objective lens sits from the cornea. The rest(s) can also be made from a deformable material such as rubber to allow contact with the rubber and the orbit of the eye for stabilization as the cornea is moved closer or further away from the objective for optimized visualization of the fundus.

In the embodiment shown in FIG. 2, a rubber eye cup 50 is attached to the ophthalmic lens 22 or to housing may be used to assist in the proper orientation of the eye with respect to the apparatus. For example, the operator can hold the ocular device 10 up to the subject's eye so that the rubber cup 50 is held stationary on the subject's orbit. The distance between lens 22 and the surface of the subject's eye (cornea) is in a range that is near the appropriate working distance as specified by the lens manufacturer to allow imaging of the subject's retina. A working distance of approximately 10 mm to approximately 15 mm is typical.

Figure 4:
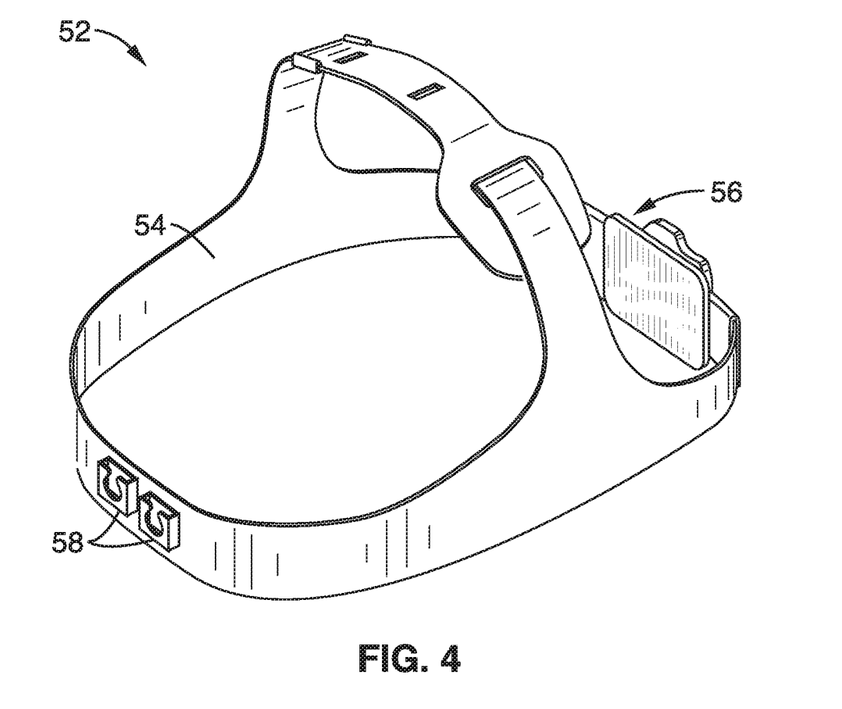
FIG. 4 is a perspective view of one embodiment of stabilizing headgear with a ratchet and adjustable headband.

In addition to the rubber cup 50 for stabilization on the subject's orbit, other methods can be used such as head gear that is similar to a conventional hard hat suspension liner that has a ratchet system that tightens a circumferential band around the head of the wearer to secure the hard hat. In the embodiment shown in FIG. 4, the head gear 52 has a preferably padded band 54 that encircles the head along with a ratchet 56 and at least one device mount 58. The head gear 52 can be placed on the subject's head and then tightened with the ratchet 56 to ensure the proper orientation of the ocular device to the eye of the subject and to stabilize the device during use. The ocular device can be mounted on the head gear 52 by clipping, mechanical mounting, hooks that encircle the suspension band, or any other mounting technique known to those skilled in the art. The ocular device can be designed to be detachable from the head gear 52 mounting system or it can be designed to be permanently attached.

Once the apparatus is generally positioned over the eye of the subject, the user can activate the light source and pre-view an image on the display 16 of the mobile device. Preview images allow the user to make small position adjustments and to focus the view before acquiring a final image. The apparatus can also use the auto-focus of the mobile device as a focusing mechanism for image acquisition.

In addition to the camera feature, the mobile device 12 also has a microprocessor and programming that can control various aspects and components of the apparatus as well as control the acquisition, processing, storage and transfer of images. In another embodiment, the images that are acquired by the apparatus are simply transferred out to a remote device for processing and storage.

The software of the mobile device 12 may have modules or programming in at least three areas, namely: (1) image acquisition; (2) image processing and storage; and (3) communications.

The image acquisition programming of the mobile device 12 provides control over the device components in the production of the initial image. For example, in one embodiment, the mobile device programming controls the actuation timing, intensity, duration and wavelength of the components of the illumination path as well as focusing, aligning, pre-viewing and final acquisition of the image.

Preview images on the display 16 of the mobile device 12 allow the user to evaluate and change the location, illumination and focus of the apparatus before the final image is acquired. Therefore, the previews that are produced by the apparatus are preferably of sufficient detail and orientation to permit adjustments.

One characteristic of the system illustrated in FIG. 1 with the use of an objective lens 22 optically coupled to a relay lens 20 coupled to a camera lens 14 of a mobile device 12 is that it creates a real, inverted image on the sensor of the mobile device 12. Due to the inverted nature of the preview on the display screen 16 of the mobile device 12, proper positioning for adequate image acquisition is more difficult because movement to the left corresponds to a right shift on the screen, and movement down corresponds to an upward screen movement. This is similar to the inverted nature of the binocular indirect ophthalmoscope.

To address this inversion, an additional lens in the imaging path is used to invert the image so that the image in the camera has the same orientation as the object in one embodiment. However, the major disadvantage of using an additional lens to invert the image is that it creates additional reflective surfaces that can add to the number of reflection artifacts as well as create scattering noise.

In another embodiment, the software on the mobile device 12 is modified to transform the real inverted image created by the ocular device into an image that appears upright to the user in display 16. In this embodiment, a dedicated software application for the processor on the mobile device 12 inverts the preview image feed on the camera sensor in real-time and displays that inverted image on the screen to allow the user/photographer to adjust the device into proper position. The preferred transformation performed by the dedicated software application is a reflection across the horizontal and vertical axes. The use of the horizontal and vertical transformation performed by the dedicated camera application creates an upright representation of the object in the preview mode that is more intuitive for the user to operate.

There are many aspects of the light source 28 that can be controlled by the programming of the mobile device 12 in those embodiments where the light source is not simply actuated by a power switch. The light source 28 can be actuated through a wired or wireless connection with the mobile device in conjunction with the mobile device battery or the power supply and circuit 40 shown schematically in FIG. 1. This enables the mobile device 12 to trigger the light source 28 to turn on in synchrony with the capturing of the retinal image. Wireless control via Bluetooth or infrared of a single-board microcontroller can also be utilized to control the LEDs.

In one embodiment, the workflow of the interface starts with the mobile device 12 sending a signal to the microcontroller to turn on a low-level light or a light with an alternate wavelength when the dedicated camera application is initiated on the mobile device 12. Once the operator obtains the desired focus and field-of-view, a second signal can be sent to the microcontroller when a button is pressed on the mobile device. This second signal can trigger a second LED to turn on or flash when the image is being captured. This is beneficial because it allows a low-level light or alternative wavelength light to be used for focusing on the retina and a (potentially separate) a high intensity light flash that can be used to capture the final image, thus minimizing the light exposure to the subject's retina.

Similarly, the mobile device 12 software programming can also control the sequence and duration of light source actuations to produce temporal and spatial illumination of the eye. The ocular imaging system can then capture images of different fields of the retina and then process and compile the images to show the entire field of the retina as one image. The LED's that are in the light source 28 may be in the "on" or "off" state in various combinations and can be activated to produce images that highlight the details of the different regions of the retina to increase resolution.

The LEDs wavelengths can also be matched to either or both of the absorption or reflectance of different components of the fundus including melanin, macular pigment, the optic disc, oxygenated blood, and deoxygenated blood. The light wavelengths of the LEDs can also be in the scotopic and photopic response range of the eye.

However, the system can also use LEDs that emit outside of the scotopic and photopic response region of the eye (LED with emissions>700 nm) to decrease pupillary constriction of the eye to allow a wider opening for imaging through the pupil or avoid the use of pharmacological dilators altogether.

Figure 5:
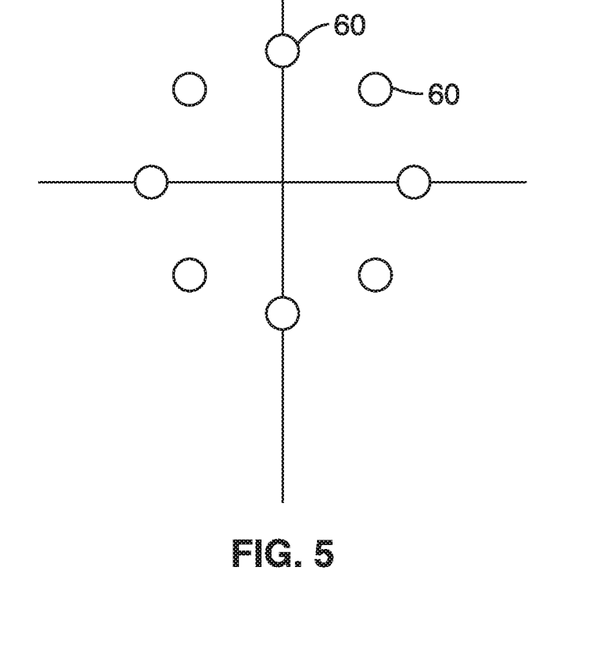
FIG. 5 is an example of a light pattern mounted off axis for subject fixation.

In another embodiment, the LED's can be placed off-axis as shown in FIG. 5 and can be illuminated by the microcontroller and programming of the mobile device 12 to provide subject fixation so that the desired retinal field-of-view is imaged. The microcontroller of the mobile device 12 sends a signal to a fixation LED 60 to turn on. The fixation LED's can be a different color than the low-level illuminating LED to allow the subject to distinguish the two. If a set of 8 LED's as shown in FIG. 5 are mounted off-axis at the same plane as the diffuser 32 or mask slit 36, the subject can be directed to look at the off-axis LED that is triggered to illuminate by the microcontroller. The microcontroller can be programmed so that only one LED is turned on at one time, and the each activated LED turns off when the next LED turns on.

Accordingly, if the microcontroller is designed to turn on one of the different off-axis LED's after each retinal image is captured, the subject will be moving the eye slightly to fixate on the newly lit LED so that each successive retinal image captures a different region of the retina. This technique enables different regions of the retina to be captured with each acquired image so that a larger view of the retina can be viewed if these images are stitched or montaged together. In addition, the microcontroller can be programmed to control which fixation LED is illuminated so that the operator can control where the subject fixates so that the desired retinal region is imaged.

In another embodiment, the built-in flash of the mobile device can be used to trigger the capture of the retinal image. If a low-light level, or alternate wavelength LED is used to focus on the retina, a photodiode can be mounted on the apparatus housing so that it sits in front of the flash of the mobile device. When the camera of the mobile device is triggered to capture an image, the flash can then initiate the photodiode, which would send a signal to a microcontroller when it detects the flash of the mobile device camera and triggers a secondary illumination source such as an LED or a combination of LEDs. If this is timed so that the mobile device acquires an image within the same time window that the secondary illumination source flashes, this would create a method of synchronizing the secondary flash with the camera capture without an electronic (wired or unwired) connection between the mobile device and the ocular device.

The acquisition software programming of the mobile device 12 can also control the focus, color balance and exposure. Light in the infra-red (IR) region can be used to focus and center the image because human eyes are not capable of sensing IR light, while the camera sensor has that capability. A white light can then be flashed to capture a final color image once the image is focused and oriented using IR light.

However, the unmodified camera sensors of many commercial mobile devices do not permit control over the color balance, white balance, and exposure. In addition to this, most camera modules on commercially available mobile devices now have infrared filters to decrease noise from IR region. To overcome this limitation on some mobile devices, the apparatus may use a monochromatic LED to illuminate the retina for fundus imaging. The LED wavelength would have specifications with a peak light intensity in the far red region (650 nm-750 nm). In this region of wavelengths, the camera is still sensitive to the light emitted and reflected off of the retina. However, the human subject is less sensitive and reactive to this wavelength region of light because it is at the extreme of the visible spectrum.

Furthermore, the intensity of the monochromic LED can be increased to match the exposure requirement needed by the white LED, so that exposure requirement of the monochromic LED will be equivalent to the exposure requirement of the subsequently flashing white LED. This technique will allow the mobile phone device to both focus and properly expose without irritating the subject being photographed. Color balance can also be achieved using a sensor with unknown and/or variable color balance and demosaicing characteristics with the use of sequential monochromatic illumination.

In one embodiment, the illumination system has a white LED configured to capture a final color image and a far red LED that is configured to be used to set the focus of the system, to provide "preview" illumination and to determine the intensity to be increased to set the exposure to the same level as the white LED. Preferably, the far red LED is chosen to have a peak or a relative intensity that is >0.75 of peak at the peak of (1-photopic response) multiplied by response of camera with filters intact (IR filter, etc).

In other words, the imaging system in this configuration uses LEDs with peak wavelengths (or wavelength that is >0.75 of relative peak wavelength intensity) at a region that is the peak of the following equation: (camera spectral response)×(reflectance of specific region of retina), thereby enabling the maximum response from specific regions of the retina. The specific regions of the retina can include the retinal vasculature (vein or artery), the optic disc, the macula, or the retinal nerve layers.

In a further embodiment, the system optionally includes an image intensifier in the imaging path. The image intensifier can be an image intensifying tube, micro-channel plates, or a thin film or similar component that is placed in the optical train of the system to convert longer wavelength light to shorter wavelength light. Accordingly, the system with the image intensifier is configured to convert IR images into images in the visible wavelength to enable a camera phone that has an IR filter to image the retina.

In various embodiments, single or multiple LEDs are controlled, related to, or based on mobile phone camera feedback through wireless (Bluetooth or Wi-Fi) or electrical connections. The feedback from the mobile device can be closed-loop using software to modify: (a) the intensity of each LED independently; or (b) the combination of LEDs turned on or off; or (c) the color balance of the image; or (d) the utilization of the dynamic range of the sensor. For example, the imaging system can use a real-time, closed-loop feedback where the software changes the intensity of the illuminating LED(s) to color balance the image before the device user sees the image in the display.

In another embodiment, the ocular imaging system can be used in conjunction with fluorescent dyes that have been introduced to the eye or the surrounding structures. The apparatus can control the wavelength, sequence and duration of LED emissions to excite one or more fluorescent dyes. The LED wavelengths will be determined by the dyes that are selected. The preferred LED wavelength emissions for use with fluorescent dyes are in the blue region (450 nm to 500 nm); the violet wavelength region (400 nm to 450 nm); and the ultraviolet (UV) wavelength region (200 nm to 400 nm).

Similarly, the imaging system can use a light source that includes a blue LED (400 nm-500 nm peak emission) to provide an image based on the autofluorescence of the retina.

Accordingly, the apparatus can have LEDs with different colors for fluorescence and brightfield imaging and a switch configured to switch between fluorescence and brightfield imaging modes.

The software programming of the apparatus can also have a processing module that generally processes the initial images acquired by the mobile device 12. For example, some embodiments of the imaging system can capture images of different fields of the retina and then process the images to compile the images to show the entire field of the retina as one image.

In another embodiment, the image processing software of the apparatus can use anatomical features (optic disk, retinal artery, vein, arteriole, or venule caliber or width, macular features including foveal reflex, distance between the optic disk and the macula, and the like) as a scale for measurement within the images. For example, the scale for measurement as a frame of reference in the captured images can be a scale that is placed in an intermediate plane in the system or a digital scale that is provided by the software.

The processing software module can also provide multispectral imaging. Here, the captured IR, far red, and color images are overlaid and compared via processing software to identify any features that are visible in one illumination wavelengths that may not be detected in the other illumination wavelengths.

The acquired and processed images may be stored in the device or on removable media. The images on the mobile device 12 may also be transmitted to a remote location for further evaluation through wired or wireless transmissions with the Wi-Fi, Bluetooth, or cellular network capabilities of the mobile device or through an Ethernet cable.

The communications module of the programming software of the mobile device can prepare and transmit to any number of remote locations for storage or real time evaluation by a third party for remote ocular evaluation (telemedicine) or for medical screening. For example, the captured and processed images can be transmitted and inserted into designated patient electronic medical records. The images can also be transmitted simultaneously to one or more physicians in different locations for a real time evaluation and diagnosis. The ocular imaging system can be used for the remote diagnosis of diseases including diabetic retinopathy, hypertensive retinopathy, glaucoma, age-related macular degeneration, macular dystrophy, retinal detachment, papilledema, macular edema, retinal detachment, retinopathy of prematurity, retinal vascular occlusions, and infectious or parasitic retinal diseases.

The technology described herein may be better understood with reference to the accompanying examples, which are intended for purposes of illustration only and should not be construed as in any sense limiting the scope of the technology described herein as defined in the claims appended hereto.

EXAMPLE 1

In order to demonstrate the operational principles of the apparatus and system, a retinal camera apparatus based on a mobile phone was constructed. The camera included a custom-designed mobile phone attachment that housed optics that were capable of capturing a retinal field-of-view of approximately 55 degrees. The device provided wide field imaging, enabling convenient and high-resolution diagnostic imaging for a broad set of applications.

The housing contained the illumination and collections optics, and an integrated phone holder that ensured alignment of the optics with the camera on the phone. The acrylonitrile butadiene styrene (ABS) plastic housing was designed and constructed for use with an iPhone 4S® mobile phone. The phone required no modification, and the mobile phone could easily slide in and out of the holder. A rubber cup on the lens eye piece rested on the orbital rim of the sitting or supine subject, providing user-controlled stabilization of the apparatus.

Retinas of human test subjects were imaged through a 54-diopter ophthalmic lens. The ophthalmic lens of the apparatus formed an intermediate image that was relayed by a 20 mm focal length achromatic lens to the 8-megapixel camera of the mobile phone. The auto-focus mechanism of the camera of the mobile phone was used to correct for the variability in axial length and refractive error in subject eyes. Images were captured using the native camera application. The scope did not have a built-in fixation method, requiring the subject to use a contralateral eye for fixation.

Illumination of the retina was provided by three white light-emitting diodes (LEDs) controlled independently from the mobile phone by an on/off dimming circuit powered by two 9-volt batteries. A 25 mm focal length collector lens was placed in front of the LEDs followed by a ground glass diffuser, a plastic linear polarizer, a matte board annular mask with a 7.0 mm inner diameter and a 15 mm outer diameter, and a 50 mm focal length condenser lens. A polarizing wire grid beam splitter was placed at a 45-degree angle to reflect the illumination towards the eye of the subject.

One property of the beam splitter is that it preferentially reflects light that is polarized parallel to its vertical axis, and transmits light that is polarized parallel to its horizontal axis. This allows vertically polarized light to be reflected towards the ophthalmic lens, which then forms an image of the annulus with a 4.5 mm inner diameter and a 9.6 mm outer diameter near the pupil of the eye. The image of the annulus blocked light at the central region of the pupil that decreased the reflection off of the central cornea. The unmasked light passed at the periphery of the pupil and then defocused to form a diffuse, uniform illumination on the retina. As the light reflected off of the retinal surface, it was depolarized, creating light polarized in both the vertical and horizontal axes relative to the beam splitter.

Light that is polarized parallel to the horizontal axis of the beam splitter is preferentially transmitted through the beam splitter. The polarized light then travels through a second polarizer that was oriented parallel to the horizontal axis of the beam splitter (perpendicular to the first plastic polarizer), and through the relay lens to the mobile phone camera. This cross-polarization technique limited reflection artifacts from the ophthalmic lens and surface of the eye.

EXAMPLE 2

To assess the potential for the device as a telemedicine tool, diagnostic quality images of diabetic retinopathy and active CMV retinitis were captured from dilated patients in Thailand and transmitted directly from the mobile phone devices to a secure server. These images were of sufficient quality to enable the remote ophthalmologist in the United States to accurately provide a real-time diagnosis of the retinal diseases.

The mobile phone-based retinal camera apparatus enabled the capture of fundus images remotely. When used through a dilated pupil, the device captures a field-of-view of approximately 55 degrees in a single fundus image. The images were captured on 2652×2448 pixel camera sensor, resulting in approximately 48 pixels per retinal degree. This surpasses the minimum image resolution requirement of 30 pixels per degree suggested by the United Kingdom Nation Health Service for diabetic retinopathy screening.

Based on initial testing with the device, the time required to capture 10 photographs from a single subject is approximately 5 minutes. If used continuously, the battery life of the device was approximately 2 to 4 hours, with the LED light source as the primary consumer of power. Consequently, the apparatus was capable of remote testing of many patients between battery chargings.

In some cases, images captured by the mobile phone-based retinal camera were also stitched together using i2k Retina software (DualAlign LLC, Clifton Park, N.Y.) to create a composite image that captured a larger field-of-view of the retina. This mosaic compared well with a mosaic created using images taken with a TRC-50EX retinal camera (Topcon Medical Systems, Oakland, N.J.) when contrast and exposure were similarly scaled.

The cross-polarization technique was also used and evaluated. Use of the technique reduced, but did not eliminate the reflection from the back surface of the ophthalmic lens. In addition, the cross-polarization technique utilized by the device was shown to increase the visibility of the choroid, optic disc, and blood vessels and also accentuate nerve fiber layer defects by reducing nerve fiber layer reflectivity.

However, the cross-polarization also decreased the specularly reflected light from the internal limiting membrane that can be helpful for photography of certain retinal pathology.

From the discussion above it will be appreciated that the technology described herein can be embodied in various ways, including the following:

1. A portable, hand-held imaging system, comprising: (a) an acquisition unit with a first set of optical elements positioned at a proximal section of the unit; a second set of optical elements spaced distally relative to the first group and aligned along an optical axis; (b) an illumination unit of at least one light source configured to illuminate a target disposed along the optical axis of the second set of optical elements: and (c) an imaging unit, comprising: (i) a camera sensor optically coupled to the first set of optical elements of the acquisition unit along the optical axis; (ii) a computer processor coupled to the camera sensor; and (iii) programming residing in a non-transitory computer readable medium, wherein the programming is executable by the computer processor and configured to capture illuminated images of the target from the camera sensor; and (iv) a memory for storing captured images of the target.

2. The imaging system of any previous embodiment, wherein the first set of optical elements of the acquisition unit comprises a polarizer and a relay lens and the second set of optical elements comprises an ophthalmic lens.

3. The imaging system of any previous embodiment, the acquisition unit further comprising a filter selected from the group of filters consisting of a glass filter, a bandpass filter, a longpass filter, and a shortpass filter.

4. The imaging system of any previous embodiment, wherein the illumination unit comprises: a plurality of light sources; a collector lens configured to collect light from the light source and focus it on the plane of a polarizer; a condenser lens to concentrate light from the polarizer onto a beam splitter disposed between the first and second optical elements and in the optical axis of the acquisition unit; wherein polarized light from the light source is divided by the beam splitter and transmitted out through the second set of optical elements to illuminate a target.

5. The imaging system of any previous embodiment, wherein the illumination unit further comprises a diffuser interposed between the collector lens and the polarizer.

6. The imaging system of any previous embodiment, wherein the illumination unit further comprises a mask interposed between the polarizer and the condenser lens.

7. The imaging system of any previous embodiment, wherein the illumination unit further comprises a power supply circuit coupled to the light source controlled by the programming of the imaging unit, wherein actuation and duration of the light source is controlled by the imaging unit computer processor programming.

8. The imaging system of any previous embodiment, wherein the light source of the illumination unit comprises one or more light emitting diodes (LED).

9. The imaging system of any previous embodiment, wherein the light source of the illumination unit comprises: one or more light emitting diodes (LED) emitting light in the far red region (650-750 nm); and one or more white light emitting diodes (LED); wherein the far red LED is configured to provide "preview" illumination; wherein the far red LED is configured to set the focus of the system; and wherein the far red LED is configured for intensity to be increased to set the exposure to the same level as the white LED.

10. The imaging system of any previous embodiment, wherein the light source of the illumination unit comprises at least one LED that emits light in a wavelength that will excite a fluorescent dye selected from the group of the blue region 450-500 nm, the violet region 400-450 nm, and the ultraviolet (UV) region 200-400 nm.

11. The imaging system of any previous embodiment, wherein the illumination unit further comprises a wireless receiver configured to receive wireless control commands from the imaging unit computer processor programming.

12. A mobile ocular imaging system, comprising: (a) an acquisition unit with a first set of optical elements positioned at a proximal section of the unit: a second set of optical elements spaced distally relative to the first group and aligned along an optical axis; (b) an illumination unit of a power supply and at least one light source configured to illuminate a target disposed along the optical axis of the second set of optical elements; (c) an imaging unit, comprising: (i) a camera sensor optically coupled to the first set of optical elements of the acquisition unit along the optical axis; (ii) a computer processor coupled to the camera sensor and illumination unit; and (iii) programming residing in a non-transitory computer readable medium, wherein the programming is executable by the computer processor and configured to capture illuminated images of the target from the camera sensor; and (iv) a memory for storing captured images of the target; and (d) a communications unit with at least one transmitter and receiver for transmitting captured and processed images and receiving data from a remote source through wired or wireless transmissions.

13. The imaging system of any previous embodiment, wherein the second optical element comprises an objective lens having a diopter selected from the group consisting of a diopter$\geq$1, a diopter$\geq$5, a diopter$\geq$10, a diopter$\geq$15, a diopter$\geq$30; and a diopter$\geq$50.

14. The imaging system of any previous embodiment, wherein the light source of the illumination unit comprises: one or more light emitting diodes (LED) emitting white light, light in the infrared region, and light in the far red region; and wherein captured IR, far red, and color images are overlaid and compared by imaging unit programming to identify any features that are visible in one illumination wavelength that may not be detected in the other illumination wavelengths thereby providing for multi-spectral imaging.

15. The imaging system of any previous embodiment, wherein the light source of the illumination unit comprises one or more light emitting diodes (LED) with emissions >700 nm that are outside the scotopic and photopic response region of the eye that decrease pupillary constriction of the eye to allow a wider opening for imaging through the pupil and to avoid the need for pharmacological dilators.

16. The imaging system of any previous embodiment, wherein the light source of the illumination unit comprises at least one blue LED with 400-500 nm peak emissions to image based on the autofluorescence of the retina.

17. The imaging system of any previous embodiment, further comprising one or more light emitting diodes are positioned off axis at a position in the optical path that provides a fixation point for the subject being photographed to fixate on to allow specific regions of the retina to be imaged.

18. The imaging system of any previous embodiment, further comprising: imaging an annulus of light at or near the eye pupil with numerical aperture (NA) selected from the group consisting of less than or equal to 0.01, less than or equal to 0.1, less than or equal to 0.25, less than or equal to 0.5; and less than or equal to 1; wherein the NA determines the depth of focus of the annulus; and wherein the annulus is focused sufficiently to penetrate the cornea, anterior compartment, and lens while in focus, but defocused by the time it gets to the retina so that the illumination is uniform.

19. The imaging system of any previous embodiment, wherein the imaging unit programming further comprises a feedback loop between the imaging unit and the illumination unit to alter image characteristics by modifying the intensity of each LED independently or controlling the combination of LEDs that are turned on or off.

20. The imaging system of any previous embodiment, wherein the imaging unit programming further comprises a feedback loop between the imaging unit and the illumination unit to determine the regions of the retina that are being imaged so that regional images can be compiled to show the entire field of the retina as one image by the imaging unit programming.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| | | | | | Mask Slit Inner Diameter | | | |
|---|---|---|---|---|---|---|---|---|
| A | b1 | b2 | C | Total Mag | 7.0 mm | 8.0 mm | 9.0 mm | 10.0 mm |
| 5.0 | 20.0 | 25.0 | 29.2 | −0.64 | 4.5 mm | 5.1 mm | 5.8 mm | 6.4 mm |
| 7.5 | 20.0 | 25.0 | 28.2 | −0.62 | 4.3 mm | 4.9 mm | 5.6 mm | 6.2 mm |
| 10.0 | 20.0 | 25.0 | 27.3 | −0.59 | 4.2 mm | 4.8 mm | 5.3 mm | 5.9 mm |
| 12.5 | 20.0 | 25.0 | 26.5 | −0.57 | 4.0 mm | 4.6 mm | 5.2 mm | 5.7 mm |
| 15.0 | 20.0 | 25.0 | 25.7 | −0.55 | 3.9 mm | 4.4 mm | 5.0 mm | 5.5 mm |
| 17.5 | 20.0 | 25.0 | 24.9 | −0.53 | 3.7 mm | 4.3 mm | 4.8 mm | 5.3 mm |
| 20.0 | 20.0 | 25.0 | 24.3 | −0.52 | 3.6 mm | 4.1 mm | 4.6 mm | 5.2 mm |
| 22.5 | 20.0 | 25.0 | 23.6 | −0.50 | 3.5 mm | 4.0 mm | 4.5 mm | 5.0 mm |

TABLE 1-continued

Mask Slit Inner Diameter

| A | b1 | b2 | C | Total Mag | 7.0 mm | 8.0 mm | 9.0 mm | 10.0 mm |
|---|---|---|---|---|---|---|---|---|
| 25.0 | 20.0 | 25.0 | 23.0 | −0.48 | 3.4 mm | 3.9 mm | 4.4 mm | 4.8 mm |
| 27.5 | 20.0 | 25.0 | 22.4 | −0.47 | 3.3 mm | 3.8 mm | 4.2 mm | 4.7 mm |
| 30.0 | 20.0 | 25.0 | 21.9 | −0.46 | 3.2 mm | 3.6 mm | 4.1 mm | 4.6 mm |

What is claimed is:

1. A portable, hand-held imaging system, comprising:
 (a) an image acquisition device comprising a polarizer and a relay lens positioned at a proximal section of the image acquisition device; and an ophthalmic lens spaced distally relative to the polarizer and relay lens and aligned along an optical axis;
 (b) an illumination device comprising at least one light source oriented to direct a light beam to illuminate an eye of a subject along the optical axis of the image acquisition device, a collector lens configured to collect light from the light source and focus it on the plane of a polarizer, and a condenser lens configured to concentrate light from the polarizer onto a beam splitter; and
 (c) a mobile device, comprising:
  (i) a camera sensor optically coupled to the ophthalmic lens, polarizer and relay lens of the image acquisition device along the optical axis;
  (ii) a computer processor coupled to the camera sensor; and
  (iii) programming residing in a non-transitory computer readable storage medium, wherein the programming is executable by the mobile device computer processor and configured to capture illuminated images of the illuminated eye of the subject from the camera sensor; and
  (iv) a computer readable storage medium to store captured images.

2. An imaging system as recited in claim 1, said acquisition device further comprising a filter aligned along the optical axis selected from the group of filters consisting of a glass filter, a bandpass filter, a longpass filter, and a shortpass filter.

3. An imaging system as recited in claim 1, wherein said illumination device further comprises:
 a plurality of light sources;
 the beam splitter disposed between the ophthalmic lens and the polarizer along the optical axis of the image acquisition device; and
 wherein polarized light from the light source is divided by the beam splitter and transmitted out through the ophthalmic lens.

4. An imaging system as recited in claim 3, wherein said illumination device further comprises a diffuser interposed between the collector lens and the polarizer.

5. An imaging system as recited in claim 4, wherein said illumination device further comprises a mask interposed between the polarizer and the condenser lens.

6. An imaging system as recited in claim 1, wherein said illumination device further comprises a power supply circuit coupled to the light source controlled by the programming of the mobile device, wherein actuation and duration of the light source is controlled by the mobile device computer processor programming.

7. An imaging system as recited in claim 6, wherein the light source of the illumination device comprises one or more light emitting diodes (LED).

8. An imaging system as recited in claim 6, wherein the light source of the illumination device comprises:
 one or more light emitting diodes (LED) emitting light in the far red region (650 nm-750 nm); and
 one or more white light emitting diodes (LED);
 wherein the far red LED is configured to provide "preview" illumination to preview images;
 wherein the far red LED is configured to set the auto-focus of the system; and
 wherein the far red LED is configured for intensity to be increased to set the exposure to the same level as the white LED.

9. An imaging system as recited in claim 6, wherein said illumination device further comprises a wireless receiver configured to receive wireless control commands from the mobile device computer processor programming.

10. An imaging system as recited in claim 1, wherein the light source of the illumination device comprises at least one LED that emits light in a wavelength that will excite a fluorescent dye selected from the group of the blue region 450 nm-500 nm, the violet region 400 nm-450 nm, and the ultraviolet (UV) region 200 nm-400 nm.

11. A mobile ocular imaging system, comprising:
 (a) an ocular acquisition device comprising a polarizer and a relay lens positioned at a proximal section of the ocular acquisition device; and an ophthalmic lens spaced distally relative to the polarizer and relay lens and aligned along an optical axis;
 (b) an illumination device comprising a power supply and at least one light source oriented to direct a light beam to illuminate an eye of a subject along the optical axis of the ocular acquisition device, a collector lens configured to collect light from the light source and focus it on the plane of a polarizer, and a condenser lens configured to concentrate light from the polarizer onto a beam splitter;
 (c) an imaging device, comprising:
  (i) a camera sensor optically coupled to ophthalmic lens, polarizer and relay lens of the ocular acquisition device along the optical axis;
  (ii) a computer processor coupled to the camera sensor and illumination unit; and
  (iii) programming residing in a non-transitory computer readable medium, wherein the programming is executable by the computer processor and configured to capture illuminated images of the illuminated eye of the subject from the camera sensor; and
  (iv) a computer readable storage medium to store captured images; and
 (d) a communications module with at least one transmitter and receiver for transmitting captured and processed images and receiving data from a remote source through wired or wireless transmissions.

12. An imaging system as recited in claim 11, further comprising an objective lens, said objective lens having a diopter selected from the group consisting of a diopter≥1, a diopter≥5, a diopter≥10, a diopter≥15, a diopter≥30; and a diopter≥50.

13. An imaging system as recited in claim 11, wherein the light source of the illumination device comprises:
    one or more light emitting diodes (LED) emitting white light, light in the infrared region, and light in the far red region; and
    wherein captured IR, far red, and color images are overlaid and compared by mobile device programming to identify any features that are visible in one illumination wavelength that may not be detected in the other illumination wavelengths thereby providing for multi-spectral imaging.

14. An imaging system as recited in claim 11, wherein the light source of the illumination device comprises one or more light emitting diodes (LED) with emissions>700 nm that are outside the scotopic and photopic response region of the eye that decrease pupillary constriction of the eye to allow a wider opening for imaging through the pupil and to avoid the need for pharmacological dilators.

15. An imaging system as recited in claim 11, wherein the light source of the illumination device comprises at least one blue LED with 400 nm-500 nm peak emissions to image based on the autofluorescence of the retina.

16. An imaging system as recited in claim 11, further comprising one or more light emitting diodes that are positioned off axis at a position in the optical path that provides a fixation point for the subject being photographed to fixate on to allow specific regions of the retina to be imaged.

17. An imaging system as recited in claim 11, further comprising:
    imaging an annulus of light at or near the eye pupil with numerical aperture (NA) selected from the group consisting of less than or equal to 0.01, less than or equal to 0.1, less than or equal to 0.25, less than or equal to 0.5; and less than or equal to 1;
    wherein the NA determines the depth of focus of the annulus; and
    wherein the annulus is focused sufficiently to penetrate the cornea, anterior compartment, and lens while in focus, but defocused by the time it gets to the retina so that the illumination is uniform.

18. An imaging system as recited in claim 11, wherein said mobile device programming further comprises a feedback loop between the mobile device and the illumination unit to alter image characteristics by modifying the intensity of each LED independently or controlling the combination of LEDs that are turned on or off.

19. An imaging system as recited in claim 11, wherein said mobile device programming further comprises a feedback loop between the mobile device and the illumination device to determine the regions of the retina that are being imaged so that regional images can be compiled to show the entire field of the retina as one image by the mobile device programming.

* * * * *